United States Patent [19]

McDougal et al.

[11] Patent Number: 4,582,055

[45] Date of Patent: Apr. 15, 1986

[54] IN VIVO DERMAL ABSORPTION METHOD AND SYSTEM FOR LABORATORY ANIMALS

[75] Inventors: James N. McDougal, Fairborn; Michael L. Gargas, Dayton; Robert A. Strohaver, Dayton; Gary W. Jepson, Dayton; Kenneth R. Thimling, Wright-Patterson AFB; Mark A. Williams, Dayton, all of Ohio

[73] Assignee: The United States of America as represented by the Secretary of the Air Force, Washington, D.C.

[21] Appl. No.: 612,776

[22] Filed: May 22, 1984

[51] Int. Cl.[4] .......... A61M 16/00

[52] U.S. Cl. .......... 128/202.12; 128/202.13; 128/203.29

[58] Field of Search .......... 128/630, 200.19, 202.12, 128/202.16, 202.13, 203.29

[56] References Cited

U.S. PATENT DOCUMENTS

| | | | |
|---|---|---|---|
| 300,246 | 6/1884 | Goldberg | 128/207.11 |
| 835,075 | 11/1906 | Mahaffy | 128/202.13 X |
| 2,385,683 | 9/1945 | Burton | 128/202.12 X |
| 3,230,577 | 1/1966 | Hughes | 17/1 |
| 3,505,998 | 4/1970 | Halstead et al. | 128/146.7 |
| 3,903,869 | 9/1975 | Bancalari | 128/202.12 |
| 3,915,165 | 10/1978 | Ranbasek et al. | 128/203.29 X |
| 4,332,244 | 6/1982 | Levy et al. | 128/205.25 |

FOREIGN PATENT DOCUMENTS

| | | | |
|---|---|---|---|
| 7805202 | 11/1978 | Netherlands | 128/202.12 |

*Primary Examiner*—Edward M. Coven

*Attorney, Agent, or Firm*—Donald J. Singer; John R. Flanagan; Bobby D. Scearce

[57] ABSTRACT

A method and system for in vivo dermal absorption testing of a laboratory animal uses a mask and harness for protecting the respiratory tract of the animal when the animal housed within a sealed chamber with a hazardous test vapor introduced in the chamber. Because of the difficulty of getting a good seal with a protective mask on a laboratory animal, this system is designed with an air leak from inside the mask into the chamber. To ensure that the test vapor does not infiltrate the mask nor leak from the chamber, the vapor is maintained at a negative pressure within the chamber as compared to the external atmospheric pressure and air is supplied to the mask for the animal to breathe at a positive pressure and at a greater rate than that needed by the animal.

7 Claims, 6 Drawing Figures

IN VIVO DERMAL ABSORPTION METHOD AND SYSTEM FOR LABORATORY ANIMALS

RIGHTS OF THE GOVERNMENT

The invention described herein may be manufactured and used by or for the Government of the United States for all governmental purposes without the payment of any royalty.

BACKGROUND OF THE INVENTION

1. Field of the Invention

The present invention broadly relates to the determination of dermal absorption of vapors and, more particularly, is concerned with a method and system for exposure of the skin of a laboratory animal, such as a rat, to vapors while protecting the animal's respiratory tract from exposure.

2. Description of the Prior Art

It is conventional practice for individuals to take steps to protect their respiratory tracts when working in environments containing hazardous chemicals. For example, workers in certain operational environments in the Air Force commonly wear respiratory masks to minimize the opportunities for pulmonary uptake of hazardous compounds and in these instances it is important to determine if dermal absorption of these vapors can be hazardous. However, up to the present time, it has not been known what hazards are involved in dermal exposure to certain toxic chemicals when an individual in wearing only respiratory protection. Chemical compounds such as hydrazine, chemical warfare agents and fuel vapors fall in this category. The cautious and prudent practice is to error on the side of wearing more protective clothing than might be necessary in the absence of a scientific basis for doing otherwise. Unfortunately, heretofore, studies which might provide some basis for deciding the extent of worker protection necessary in environments containing various hazardous chemicals have generally been lacking.

At the present time no satisfactory system exists to investigate the penetration of the skin by gasses or vapors. Previous approaches to investigate dermal absorption of vapors in rodents have involved isolation of the head of the rodent in a separate chamber from the body using a rubber dam to separate the chambers. These attempts have been unsatisfactory because of the tendency of the rodent to struggle when restrained by the neck and because of the difficulty in completely preventing leaks of the chemical atmosphere from the body side of the chamber to the head side of the chamber.

Consequently, a need exists for a testing setup which would reliably and accurately determine the rate of dermal absorption in laboratory animals of various hazardous chemicals, without exposure via the animal's respiratory tract.

SUMMARY OF THE INVENTION

The present invention provides a method and system of in vivo dermal absorption testing of laboratory animals, such as rats, which is designed to satisfy the aforementioned needs. Previously, it has not been possible to determine the rate of absorption of vapors and gases through intact skin because the respiratory tract is a one to two order of magnitude better route of absorption and a very small amount of vapor absorbed through the lungs invalidates results. The invention solves the problem of determining the rate of dermal absorption by isolating and protecting the respiratory tract of the animal from absorption of vapors. Pulmonary isolation is guaranteed in a unique manner in the present invention by a desired air leak around the protective mask which is a result of the combined use of a sealed chamber in which the vapor under test is maintained at a slight negative pressure, and of a protective mask secured in place on the head of the animal housed in the chamber and through which life-sustaining air is supplied to the animal at a positive pressure. The designed-in leak eliminates the possibility of infiltration of the vapor into the mask by assuring that leaks in the mask are from the mask to the chamber rather than vice versa.

Accordingly, the present invention is directed to an in vivo dermal absorption method and system for laboratory animals which basically includes the operative steps of: (a) applying a mask on a head of a laboratory animal, such as a rat, which mask protectively covers the eyes, nose and mouth of the animal; (b) housing the animal with the applied mask in a sealed chamber; (c) maintaining a test vapor within the chamber at a predetermined negative pressure as compared to atmospheric pressure external to the chamber, with the skin of the animal being exposed to the vapor; and (d) supplying life-supporting air at a positive pressure to the mask applied to the animal's head so as to preclude infiltration of the vapor into the mask. Furthermore, the vapor within the chamber is monitored so as to maintain it at a predetermined concentration. Additionally, the blood of the laboratory animal is sampled to monitor the level of the vapor absorbed therein.

Also, the present invention is directed to the combination of the head mask and a harness fitted about the forelimbs and shoulders of the animal and attached to the mask to hold the mask in its desired position on the animal's head. The head mask is formed of molded latex material adapted to fit over the animal's head so as to cover at least the nose, mouth and jaw of the animal. Preferably, the mask also covers the eyes of the animal because in rodents, covering the head and eyes calms them down. At its forward portion in front of the animal's nose, the mask has a void or dead space into which the air is supplied under positive pressure through a pair of openings formed in the mask forward portion. Of the air not inhaled by the animal, approximately 50 percent blows past the animal's nose and exits the posterior of the mask at sides of the animal's head. The other 50 percent (depending on the fit of the mask) exits through the exhaust tube in the mask. A pair of tubes can be inserted into the openings of the mask, one for supplying breathing air therein from outside the chamber and the other to exhaust excess breathing air into the room. Finally, a pair of tape segments are attached to the mask along the exterior thereof at the locations of the forehead and throat of the animal when the mask is applied to its head. The tape is preferably made from nylon fastener fabric which has either hook material or pile material on it.

The harness includes a pair of body straps and a pair of attachment straps connected therewith at upper and lower overlapped portions of the body straps. The body and attachment straps are also made from nylon fastener fabric with complementary hook and pile materials thereon. Holes are cut in the body straps at their lower overlapped portions. The forelimbs of the animal extend through the holes when the straps have been assembled together and fastened about the forelimbs and shoulders of the animal. Once the animal is fitted with the harness, the attachment straps are applied to the upper and lower tape segments on the mask so as to retain the mask on the animal's head.

DETAILED DESCRIPTION OF THE PREFERRED EMBODIMENT

Figure 1:
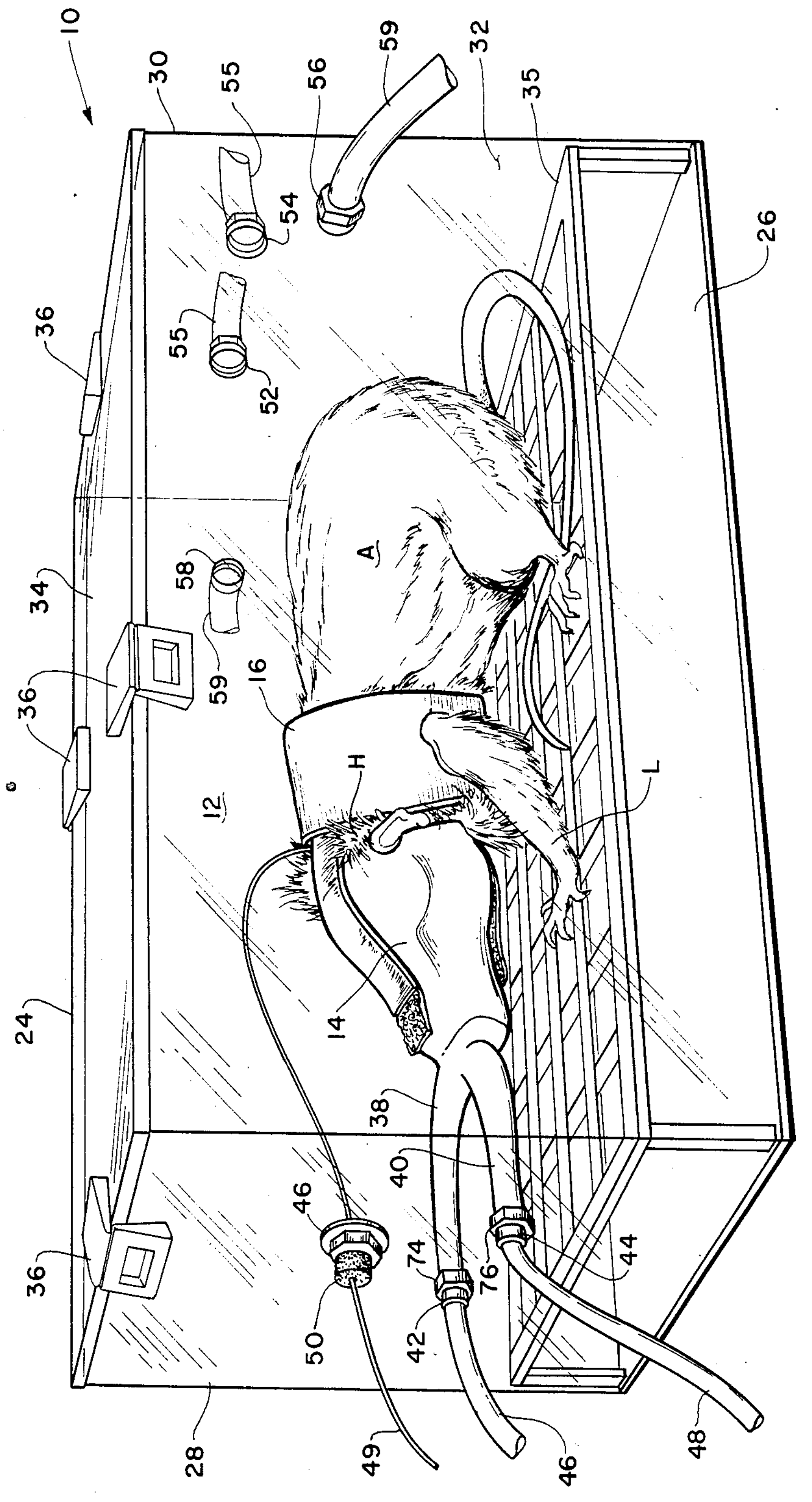
FIG. 1 is a perspective view of a laboratory animal, such as a rat, housed in a sealed chamber with the mask and harness of the present invention applied to the rat's head for carrying out the in vivo dermal absorption testing method and system of the present invention.
Figure 6:
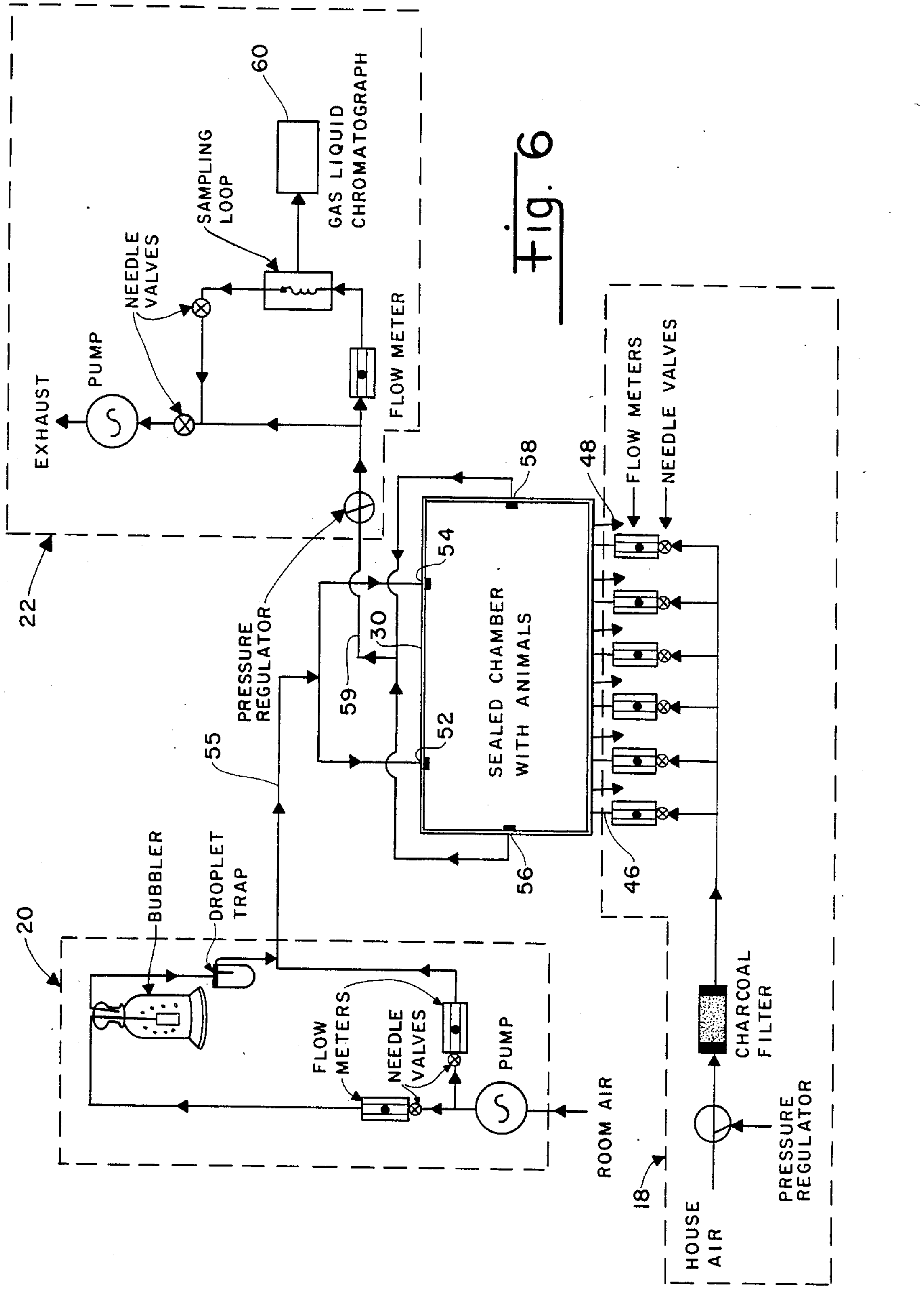
FIG. 6 is a schematic diagram of the system of the present invention for carrying out in vivo dermal absorption testing on the laboratory animal.

Referring now to the drawings, and more particularly to FIGS. 1 and 6, there is shown the preferred embodiment of the in vivo dermal absorption testing system of the present invention, being generally designated by the numeral 10. The dermal absorption testing system 10 basically includes a sealed chamber 12, a mask 14 applied to the head H of an animal, such as a rat A, housed in the chamber, a harness 16 fitted on the rat to retain the mask 14 on the animal's head H, a source 18 of air supply to the animal through the mask 14, apparatus 20 for generating the vapor atmosphere within the sealed chamber 12, and apparatus 22 for monitoring the atmosphere within the sealed chamber 12.

The chamber 12 has top and bottom walls 24,26 and pairs of end and side walls 28,30 and 32,34 extending upright between the top and bottom walls. The end and side walls 28,30 and 32,34 are rigidly interconnected together and with the bottom wall 26 to form a box-like structure having an open top. The top wall 24 is adapted to be placed on the top edges of the interconnected end and side walls 28,30 and 32,34 in order to close the open top and then be sealed thereto by actuation of locking clasps 36 on the peripheral edges of the top wall 24 and the top edges of the respective end and side walls. The walls are preferably made of transparent, acrylic material. For purposes of simplicity, only a single chamber 12 with a single animal A is illustrated in FIG. 1. However, it will readily apparent that a larger chamber for housing multiple animals in individual compartments separated, for example, by wire mesh dividers or partitions is more desirable.

The animal A with the mask 14 applied to its head H is fastened in the chamber 12 by attachment of inlet and exhaust tubular segments 38,40 of the mask 14 to fittings 42,44 mounted in the front end wall 28 of the chamber 12. An air supply tube 46 is connected to a suitable air supply 18, and extends through the fitting 42 and tubular segment 38 of the mask 14 for communicating air to the mask for the animal to breathe. Exhaust air travels through the exhaust segment 40, fitting 44 and exhaust tube 48 which is open to the room. In addition, the front end wall 28 of the chamber 12 has another fitting 46 through which extends the jugular catheter 49 which enters the rodent's body at the back of the neck and is used to serially sample blood from the animal. The fitting 46 is made air tight by use of a cork and silicone sealant 50. Blood is drawn from the jugular cannula 49 at regular intervals and analyzed by any method desired. Finally, a pair of inlet ports 52,54 are provided in the rear end wall 30 for connecting the chamber 12 via a line 55 to the chamber vapor atmosphere generation apparatus 20, and a pair of outlet ports 56,58 are provided in the side walls 32,34 for connecting the chamber via line 59 to a gas chromatograph sampling apparatus 60 of the atmosphere monitoring apparatus 22 which analyzes the concentration of vapor in the chamber 12.

Figure 5:
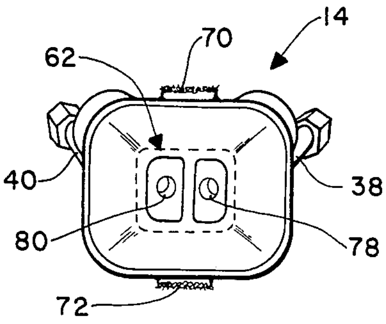
FIG. 5 is an end elevational view of the head mask taken along line 5—5 in FIG. 4.
Figure 4:
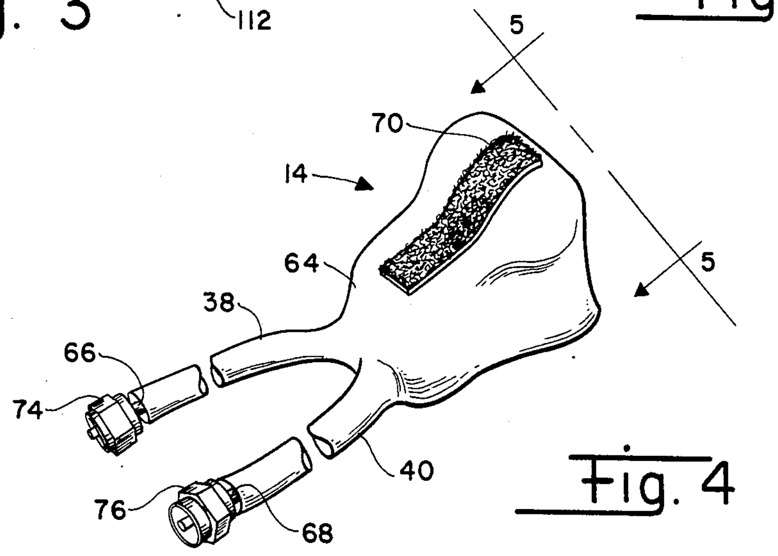
FIG. 4 is a perspective view of the animal head mask of the present invention.

As seen in FIGS. 4 and 5 as well as in FIG. 1, the mask 14 is formed of molded latex material adapted to fit over the animal's head so as to cover at least the nose, mouth and jaw of the animal. Preferably, the mask also covers the eyes of the animal. This seems to have a calming effect on the behavior of the rat. Parenthetically, it should also be mentioned here that the animal will undergo training for approximately three eight-hour periods to accustom the animal to wearing the mask 14 and harness 16 before the animal is used in actual testing.

The mask 14 is preferably fabricated by a two step process. First, an impression of a rat head is made by dipping the head into dental impression material and then a plaster cast is formed. The plaster cast is modified by adding more material to form a small void or dead space 62 (FIG. 5) at the front portion 64 of the mask around where the nose of the animal fits into the mask. The plaster cast is further modified by attaching Teflon ® tubing to form the tubular segments 38,40 constituting the air lines. The modified cast is then dipped in latex and dried in a 150 degree C. oven three times. When cured, the mask 14 is completed by attaching Teflon ® tubing 66,68 in the tubular segments 38,40 of the mask 14 and by attaching Velcro ® fastening fabric tape segments 70,72 to the exterior of the mask at the locations of the forehead and throat of the animal when the mask is applied to its head H. Nuts 74,76 are also coupled to the ends of the tubing 66,68 for use in attaching the tubing to the fittings 42,44 on the end wall 28. Opposite ends of the tubing 66,68 are inserted approximately one inch into the tubular segments 38,40 at the front portion 64 of the mask and joined thereto. The air supply 18 communicates wiht the interior of the mask 14 via the air supply tube 46, tubing 66, and tubular segment 38 through an inlet opening 78 in the front portion 64 of the mask 14. Exhaust air communicates from the interior of the mask 14 via the tube 48, tubing 68, and tubular segment 40 through an exhaust opening 80 in the front portion 64 of the mask 14.

Figure 2:
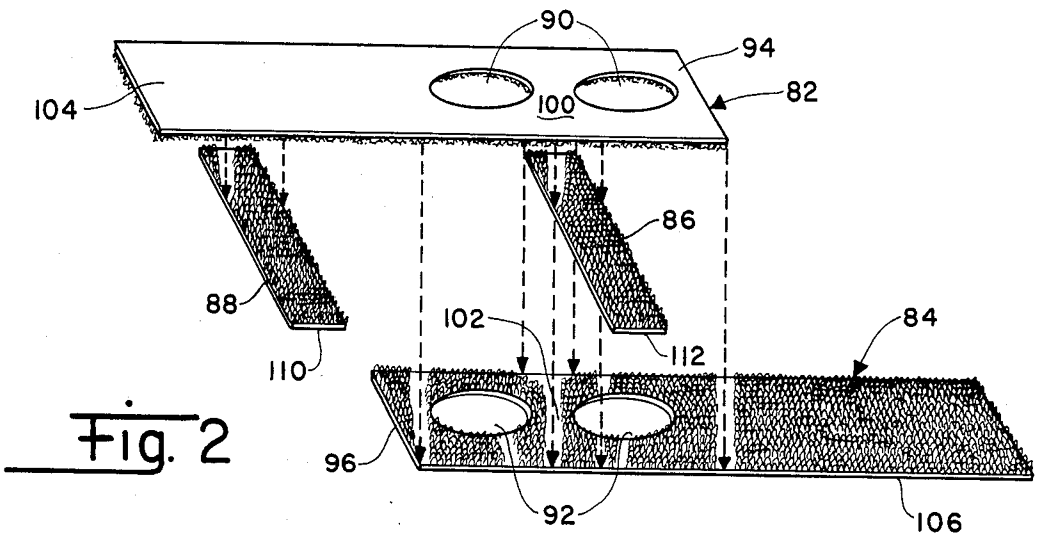
FIG. 2 is a perspective exploded view of the animal harness of the present invention in an unassembled form.
Figure 3:
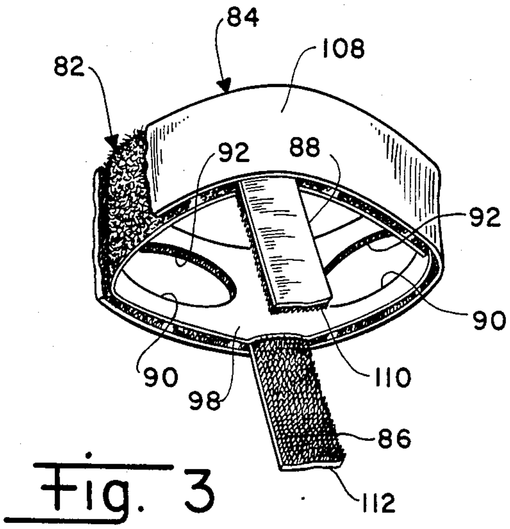
FIG. 3 is a perspective view of the animal harness in an assembled form as it would appear when fitted on the animal.

Referring now to FIGS. 2 and 3 as well as to FIG. 1, the harness 16 made from Velcro ® nylon fastener fabric is illustrated in unassembled and assembled form, respectively. The harness 16 includes a pair of body straps 82,84 and a pair of attachment straps 86,88. As seen in FIG. 2, the upper body strap 82, which becomes the inner body strap in FIG. 3, has pile material on its downwardly-facing surface. On the other hand, the lower body strap 84, which becomes the outer body strap in FIG. 3, has hook material on its upwardly-facing surface. Two pairs of holes 90,92 are cut in the respective body straps 82,84. The pairs of holes 90,92 line up with one another when the inner portion 94 of upper strap 82 containing the pile material is laid over the inner portion 96 of the lower strap 84 containing the hook material so as to form a lower overlapped region 98 of the harness 16, as seen in FIG. 3. The multiplicity of small hooks tangle with the small piles in a manner similar to an adhesive. However, the straps can be "ripped" apart and pressed back together again as many times as desired.

Before bringing the two inner portions 94,96 of the body straps 82,84 together, one attachment strap 86 is placed between the inner strap portions in alignment with the web regions 100,102 extending between the pairs of holes 90,92, such as seen in FIG. 2. The attachment strap 86 has hook material on its upwardly-facing surface which adheres to the pile material on the upper body strap 82. The other attachment strap 88 is placed adjacent an outer portion 104 of upper strap 82 before bringing portion 104 of strap 82 together with an outer portion 106 of lower strap 84 to form an upper overlapped region 108 of the harness 16, as seen in FIG. 3. The other attachment strap 88 likewise has hook material on its upwardly-facing surface, as seen in FIG. 2, which adheres to the pile material on the upper body strap 82. The upwardly-facing surface of strap 88 in FIG. 2 becomes a downwardly-facing surface in FIG. 3 once the harness is assembled.

Of course, the forelimbs L of the animal are inserted through the aligned holes 90,92 of the lower overlapped region 98 of the harness 16 before the outer portions 104,106 of the body straps 82,84 are brought together over the shoulders of the animal and formed into the upper overlapped region 108. Once the harness 16 has been assembled on the animal and the mask 14 applied to the animal's head H, the forwardly-extending portions 110,112 of the respective attachment straps 86,88 can be laid over the respective upper and lower tape segments 70,72 on the mask and pressed into attachment therewith. The tape segments 70,72 contain pile material thereon to which the hook material on the attachment straps 86,88 will adhere.

Maintenance of the test vapor within the sealed chamber 12 at a negative (i.e., subatmospheric) pressure ensures that any potential leak which might happen will result in flow of air from outside of the chamber into the chamber through the location of the leak, instead of vice versa. Also, the positive pressure (relative to the pressure within chamber 12 of the air supplied to the mask, such as at a rate of 235-250 milliliters per minute, ensures that the test vapor does not infiltrate into the mask. Instead, since the animal (as in the case of a rat) only breathes about 80 milliliters per minute of the air supplied, part of the excess air blows past the animal's head into the chamber at the posterior edge of the mask 14 and the rest goes out the exhaust tube 48. Since this air flow into the chamber reduces the concentration of the test vapor therein, the concentration of the chamber atmosphere must be continuously monitored by the chromatograph 60 of the vapor monitoring apparatus 22 so that readjustments can be made throughout the testing period.

It is thought that the invention and many of its attendant advantages will be understood from the foregoing description and it will be apparent that various changes may be made in the form, construction and arrangement of the parts and steps thereof without departing from the spirit and scope of the invention or sacrificing all of its material advantages, the form hereinbefore described being merely a preferred or exemplary embodiment.

Having thus described the invention, what is claimed is:

1. A method for determining the in vivo dermal absorption of a test vapor by the skin of a laboratory animal, comprising the steps of:

(a) applying a mask on the head of said animal, to protectively cover the eyes, nose and mouth of said animal, and applying a harness to the forebody of said animal to retain said mask on said animal's head;

(b) housing said animal with said applied mask and harness in a substantially sealed chamber;

(c) inserting said test vapor at predetermined concentration into said chamber to a predetermined pressure lower than atmospheric pressure external to said chamber, with said skin of said animal exposed to said vapor, and monitoring the concentration of said vapor within said chamber; and (d) supplying life-supporting air at a pressure higher than said predetermined pressure within said chamber to said mask applied to said animal's head to preclude infiltration of said vapor into said mask.

2. The method as recited in claim 1, wherein said applying step includes training said animal prior to testing by subjecting said animal to a plurality of periods, each several hours in length, during which said animal wears said mask and harness to become accustomed thereto.

3. The method as recited in claim 1, further comprising the step of:

(e) sampling the blood of said animal within said chamber during the exposure to monitor the level of said vapor absorbed therein.

4. A system for determining the in vivo dermal absorption of a test vapor by the skin of a laboratory animal, comprising:

(a) a mask for application on the head of said animal, to protectively cover the eyes, nose and mouth of said animal;

(b) a harness for application on the forebody of said animal and attachable to said mask to retain said mask on said animal's head;

(c) a substantially sealed chamber for housing said animal with said mask and harness applied thereto;

(d) a source of said test vapor operatively connected to said chamber for selectively supplying said test vapor at predetermined concentration to said chamber;

(e) means for maintaining said test vapor within said chamber at a predetermined pressure lower than atmospheric pressure external to said sealed chamber, said skin of said animal when housed in said chamber being exposed to said vapor;

(f) means for monitoring the concentration of said vapor within said chamber; and (g) means for supplying life-supporting air at a pressure higher than said predetermined pressure within said chamber to said mask when applied to said animal's head to preclude infiltration of said vapor into said mask.

5. The system as recited in claim 4, further comprising:

(h) means for sampling the blood of said animal during the exposure in said sealed chamber to determine the level of said vapor absorbed in said blood.

6. Apparatus for protecting a laboratory animal during in vivo dermal absorption testing of hazardous vapors, comprising:

(a) a mask adapted to fit on the head of said animal to cover the eyes, nose and mouth of said animal, said mask having opening means defined in a front portion thereof at the nose of said animal when said mask is applied to said animal through which air can be supplied to the interior of said mask; and (b) a harness adapted to fit about the forebody of said animal with the forelimbs extending through said harness, said harness being attachable to said mask to retain said mask on said head of said animal, said harness including:

a pair of body straps formed from nylon fastener fabric with one of said straps having pile material thereon and the other said strap having hook material thereon;

each of said body straps have a pair of holes cut therein for accommodating said forelimbs of said animal when said harness is applied thereto;

first end portions of said body straps forming a first overlapped region containing said holes and receiving said forelimbs of said animal therethrough when said straps are assembled together into said harness and applied to said animal; and second end portions of said body straps forming a second overlapped region opposite from said first overlapped region and extending over the shoulders of said animal when said body straps are assembled together into said harness and applied to said animal, a pair of attachment straps formed of nylon fastener fabric with one of said pile and hook materials thereon;

one of said straps being assembled between said first overlapped region formed by said first end portions of said body straps and the other of said straps being assembled between said second overlapped region formed by said second end portions of said body straps; and each of said attachment straps having attaching portions extending from said overlapped regions of said assembled body straps.

7. The protecting apparatus as recited in claim 6, wherein said mask includes:

upper and lower tape segments formed of nylon fastener fabric and attached to portions of said mask adjacent the forehead and throat of said animal when said mask is applied thereto, said segments having the other of said pile and hook materials thereon opposite to that which is contained on said attachment straps, said attaching portions of said attachment straps being attachable to said segments to retain said mask on said animal's head when both said mask and harness are applied to said animal.

* * * * *